(12) United States Patent
Blue (10) Patent No.: US 11,426,200 B2
(45) Date of Patent: Aug. 30, 2022

(54) OPERATING HANDLE FOR SELECTIVE DEFLECTION OR ROTATION OF A CATHETER

(71) Applicant: St. Jude Medical, Cardiology Division, Inc., St. Paul, MN (US)

(72) Inventor: Jeremiah Blue, Andover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 291 days.

(21) Appl. No.: 16/720,407

(22) Filed: Dec. 19, 2019

(65) Prior Publication Data

US 2020/0205856 A1 Jul. 2, 2020

Related U.S. Application Data

(60) Provisional application No. 62/785,970, filed on Dec. 28, 2018.

(51) Int. Cl.
*A61B 17/34* (2006.01)
*A61B 17/00* (2006.01)
(Continued)

(52) U.S. Cl.
CPC ...... *A61B 17/3468* (2013.01); *A61B 2017/00323* (2013.01); *A61M 25/0136* (2013.01); *A61M 2025/015* (2013.01); *A61N 1/362* (2013.01)

(58) Field of Classification Search
CPC ............... A61B 17/34; A61B 17/3468; A61B 2017/00323; A61B 19/201;
(Continued)

(56) References Cited

U.S. PATENT DOCUMENTS 3,657,744 A 4/1972 Ersek
4,423,730 A 1/1984 Gabbay
(Continued)

FOREIGN PATENT DOCUMENTS

DE 102005003632 A1 8/2006
EP 1129744 A1 9/2001
(Continued)

OTHER PUBLICATIONS

Ruiz, Carlos, Overview of PRE-CE Mark Transcatheter Aortic Valve Technologies, Euro PCR dated May 25, 2010.
(Continued)

*Primary Examiner* — Vi X Nguyen
(74) *Attorney, Agent, or Firm* — Wei & Sleman LLP (57) ABSTRACT

A delivery device 100 includes a catheter assembly 120 and an operating handle 130. The operating handle 130 may include a nose 131 affixed to the catheter assembly 120, an axial shaft 180, a base 132 translationally fixed to a proximal end of the axial shaft, a screw 160 having external threads and a non-circular lumen 161, the axial shaft extending through the non-circular lumen, a proximal end 171 of a pull wire 170 being affixed to the screw, a knob 150 having internal threads engaged with the external threads of the screw, and a collar 140 extending at least partially around the axial shaft. When the collar 140 is in a proximal position, rotation of the knob 150 may deflect the distal end 121 of the catheter assembly 120. When the collar is in a distal position, rotation of the knob 150 may rotate the catheter assembly 120.

6 Claims, 3 Drawing Sheets

(51) Int. Cl.
*A61M 25/01* (2006.01)
*A61N 1/362* (2006.01)

(58) Field of Classification Search
CPC ..... A61B 2019/208; A61N 2001/0578; A61M 25/0136
See application file for complete search history.

(56) References Cited

U.S. PATENT DOCUMENTS

| | | | |
|---|---|---|---|
| 5,078,720 A | 1/1992 | Burton et al. | |
| 5,415,664 A | 5/1995 | Pinchuk | |
| 5,484,444 A | 1/1996 | Braunschweiler et al. | |
| 5,702,418 A | 12/1997 | Ravenscroft | |
| 5,824,041 A | 10/1998 | Lenker et al. | |
| 5,843,167 A | 12/1998 | Dwyer et al. | |
| 5,924,424 A | 7/1999 | Stevens et al. | |
| 5,968,068 A | 10/1999 | Dehdashtian et al. | |
| 5,980,533 A | 11/1999 | Holman | |
| 6,077,297 A | 6/2000 | Robinson et al. | |
| 6,269,819 B1 | 8/2001 | Oz et al. | |
| 6,306,141 B1 | 10/2001 | Jervis | |
| 6,346,074 B1 * | 2/2002 | Roth | A61F 2/2427 606/213 |
| 6,391,050 B1 | 5/2002 | Broome | |
| 6,468,299 B2 | 10/2002 | Stack et al. | |
| 6,554,794 B1 | 4/2003 | Mueller et al. | |
| 6,623,518 B2 | 9/2003 | Thompson et al. | |
| 6,814,746 B2 | 11/2004 | Thompson et al. | |
| 6,830,584 B1 | 12/2004 | Seguin | |
| 7,018,406 B2 | 3/2006 | Seguin et al. | |
| 7,311,730 B2 | 12/2007 | Gabbay | |
| 7,510,572 B2 | 3/2009 | Gabbay | |
| 7,682,390 B2 | 3/2010 | Seguin | |
| 7,803,185 B2 | 9/2010 | Gabbay | |
| 8,840,663 B2 | 9/2014 | Salahieh et al. | |
| 9,168,043 B2 * | 10/2015 | van der Burg | A61B 17/12136 |
| 2003/0050694 A1 | 3/2003 | Yang et al. | |
| 2004/0210304 A1 | 10/2004 | Seguin et al. | |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2006/0074484 A1 | 4/2006 | Huber | |
| 2006/0106415 A1 | 5/2006 | Gabbay | |
| 2006/0142848 A1 | 6/2006 | Gabbay | |
| 2006/0167468 A1 | 7/2006 | Gabbay | |
| 2006/0259120 A1 | 11/2006 | Vongphakdy et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0073391 A1 | 3/2007 | Bourang et al. | |
| 2007/0088431 A1 | 4/2007 | Bourang et al. | |
| 2007/0112422 A1 | 5/2007 | Dehdashtian | |
| 2007/0162100 A1 | 7/2007 | Gabbay | |
| 2007/0168013 A1 | 7/2007 | Douglas | |
| 2007/0203575 A1 | 8/2007 | Forster et al. | |
| 2007/0239271 A1 | 10/2007 | Nguyen | |
| 2007/0244552 A1 | 10/2007 | Salahieh et al. | |
| 2008/0071369 A1 | 3/2008 | Tuval et al. | |
| 2008/0147182 A1 | 6/2008 | Righini et al. | |
| 2009/0054975 A1 | 2/2009 | del Nido et al. | |
| 2010/0004740 A1 | 1/2010 | Seguin et al. | |
| 2010/0286768 A1 | 11/2010 | Alkhatib | |
| 2010/0298931 A1 | 11/2010 | Quadri et al. | |
| 2011/0224678 A1 | 9/2011 | Gabbay | |
| 2012/0203169 A1 | 8/2012 | Tegg | |
| 2013/0131592 A1 | 5/2013 | Selkee | |
| 2014/0135745 A1 | 5/2014 | Stenzel et al. | |
| 2014/0309683 A1 | 10/2014 | Bagwell et al. | |
| 2016/0158545 A1 | 6/2016 | Khairkhahan et al. | |
| 2016/0220369 A1 | 8/2016 | Chalekian et al. | |
| 2016/0338864 A1 | 11/2016 | Vad et al. | |

FOREIGN PATENT DOCUMENTS

| | | |
|---|---|---|
| EP | 1157673 A2 | 11/2001 |
| EP | 1 926 455 A2 | 6/2008 |
| WO | 02067782 A2 | 9/2002 |
| WO | 07071436 A2 | 6/2007 |
| WO | 08070797 A2 | 6/2008 |
| WO | 10051025 A1 | 5/2010 |
| WO | 10087975 A1 | 8/2010 |

OTHER PUBLICATIONS

"Percutaneous Aortic Valve Replacement: Resection Before Implantation", Quaden, Rene et al., European J. of Cardio-Thoracic Surgery, vol. 27, No. 5, May 2005, pp. 836-840.

International Search Report including Written Opinion for PCT/US2019/067443 dated Mar. 19, 2020; 12 pages.

* cited by examiner

OPERATING HANDLE FOR SELECTIVE DEFLECTION OR ROTATION OF A CATHETER

CROSS-REFERENCE TO RELATED APPLICATIONS

This application claims the benefit of the filing date of U.S. Provisional Patent Application No. 62/785,970, filed on Dec. 28, 2018, the disclosure of which is hereby incorporated herein by reference.

BACKGROUND OF THE INVENTION

The present invention is related to implantable medical devices and, more particularly, to systems and methods for implanting a medical device.

Numerous medical devices exist today, including but not limited to implantable pacemakers, implantable cardioverter-defibrillators ("ICDs"), and the like. Medical devices of this type that are implantable (hereinafter, generally "implantable medical devices" or "IMDs") are configured to be implanted within the patient anatomy and commonly employ one or more leads with electrodes that either receive or deliver voltage, current or other electromagnetic pulses (generally "energy") from or to an organ and/or tissue for diagnostic and/or therapeutic purposes.

Typically, an intra-cardiac IMD or a lead coupled to an IMD is introduced into the heart through a catheter-based delivery device. In general, the IMD may be connected to the delivery device in a docked state in which the IMD is securely attached to a catheter of the delivery device. In the docked state, the delivery device may be operated to guide the IMD to an implant site. Once the IMD is proximate to the implant site, the delivery device may be used to torque the IMD into patient tissue.

Once the IMD is secured in patient tissue, the IMD may be moved into a tethered state with respect to the delivery device. In the tethered state, the IMD is deployed from the delivery device, but remains connected thereto. In one known system and method, two separate and distinct tethers connect the IMD to the catheter of the delivery device in the tethered state. An implanting physician may test the IMD in the tethered state to make sure that the IMD is securely and electrically connected to patient tissue at a desired location. If the physical and/or electrical connection between the IMD and the patient tissue is less than optimal, the IMD may be re-docked to the catheter of the delivery device so that the IMD may be moved to a better implanted position.

Once the implanting physician is satisfied with the location of the IMD within the patient anatomy, the IMD is transitioned from the tethered state to a released state. In the released state, the IMD is disconnected from the catheter of the delivery device.

Despite the various improvements that have been made to delivery systems for IMD leads, conventional systems suffer from some shortcomings. An IMD lead may rely on a helical, screw-in anchoring system that is used to affix the IMD lead to target tissue, such as the inside of the heart wall. During the implantation procedure, an implanting physician may need to deflect and/or rotate the distal end of the catheter of the delivery device so that the IMD lead can be affixed to the desired location. It may be difficult to accurately rotate the catheter of a conventional delivery device to place the IMD lead at the desired location and rotational orientation, which may result in inadvertent translation of the distal end of the catheter.

There therefore is a need for further improvements to the devices, systems, and methods for transcatheter delivery of IMD leads, and in particular, for transcatheter delivery of pacemaker leads. Among other advantages, the present invention may address one or more of these needs.

BRIEF SUMMARY OF THE INVENTION

The disclosure herein describes multiple embodiments of a delivery device for an implantable medical device. The delivery device may include a catheter assembly having a proximal end, a distal end, and a compartment at the distal end for retaining the implantable medical device. The catheter assembly may extend along a first longitudinal axis. The catheter assembly may have a pull wire extending therethrough. A distal end of the pull wire may be affixed to the distal end of the catheter assembly. The delivery device may include an operating handle extending along a second longitudinal axis.

The operating handle may include a nose affixed to a proximal end of the catheter assembly, an axial shaft having a distal end affixed to the nose and a proximal end, a base translationally fixed to the proximal end of the axial shaft, a screw having external threads and a non-circular lumen, a knob having internal threads engaged with the external threads of the screw, the knob being translationally fixed to the nose, and a collar extending at least partially around the axial shaft in a circumferential direction. The axial shaft may extend along the second longitudinal axis. The axial shaft may extend through the non-circular lumen so that the screw is translatable along the axial shaft and nonrotatable relative to the axial shaft. A proximal end of the pull wire may be affixed to the screw.

The collar may be rotationally fixed to the nose, the axial shaft, and the screw. The collar may be translatable between a proximal position and a distal position. With the collar in the proximal position, the knob may be rotatable relative to the collar and the collar may be nonrotatable relative to the base, so that rotation of the knob about the second longitudinal axis results in deflection of the distal end of the catheter assembly away from the first longitudinal axis. With the collar in the distal position, the base may be rotatable relative to the collar and the collar may be nonrotatable relative to the knob, so that rotation of the knob about the second longitudinal axis results in rotation of the catheter assembly about the second longitudinal axis.

Also described herein are multiple embodiments of an operating handle configured to be coupled to a catheter assembly. The operating handle may include a nose configured to be affixed to a proximal end of the catheter assembly, an axial shaft having a distal end affixed to the nose, a proximal end, and a longitudinal axis, a base translationally fixed to the proximal end of the axial shaft, a screw having external threads and a non-circular lumen, a knob having internal threads engaged with the external threads of the screw, and a collar extending at least partially around the axial shaft in a circumferential direction. The axial shaft may extend through the non-circular lumen so that the screw is translatable along the axial shaft and nonrotatable relative to the axial shaft. The knob may be translationally fixed to the nose.

The collar may be rotationally fixed to the nose, the axial shaft, and the screw. The collar may be translatable between a proximal position and a distal position. With the collar in the proximal position, the knob may be rotatable relative to the collar and the collar may be nonrotatable relative to the base, so that rotation of the knob about the longitudinal axis results in translation of the screw along the axial shaft. With the collar in the distal position, the base may be rotatable relative to the collar and the collar may be nonrotatable relative to the knob, so that rotation of the knob about the longitudinal axis results in rotation of the nose, the axial shaft, the screw, and the collar relative to the base.

Further described herein are multiple embodiments of a method of moving a catheter assembly with an operating handle. The method may include providing the catheter assembly and the operating handle. The operating handle may have a nose affixed to a proximal end of the catheter assembly, an axial shaft having a distal end affixed to the nose, a base translationally fixed to a proximal end of the axial shaft, a screw having external threads and a non-circular lumen, the axial shaft extending through the non-circular lumen, a pull wire extending from the screw to a distal end of the catheter assembly, a knob having internal threads engaged with the external threads of the screw, and a collar extending at least partially around the axial shaft in a circumferential direction.

The method may include moving the collar to a distal position relative to the base. The method may include, while the collar is in the distal position, rotating the knob in a first direction to rotate the catheter assembly, the nose, the axial shaft, the screw, and the collar relative to the base. The method may include moving the collar to a proximal position. The method may include, while the collar is in the proximal position, rotating the knob in the first direction to pull the pull wire in a proximal direction, thereby deflecting the distal end of the catheter assembly away from a longitudinal axis of the catheter assembly.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user. As used herein, the terms "generally," "substantially," "approximately," and "about" are intended to mean that slight deviations from absolute are included within the scope of the term so modified.

Figure 1A:
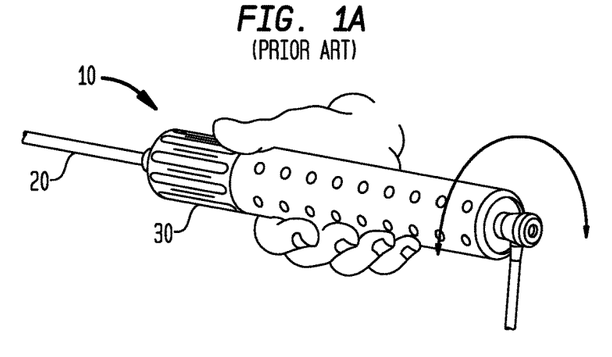
FIG. 1A is a perspective view of an operating handle of a conventional delivery device for delivering a lead for an implantable medical device (IMD) into a patient.
Figure 1B:
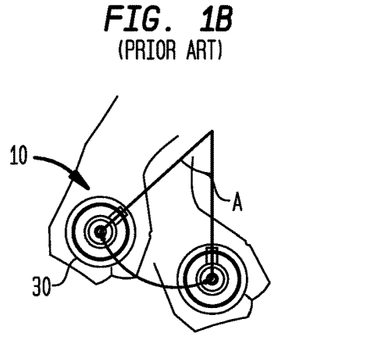
FIG. 1B is an end view of the operating handle of FIG. 1A.

FIGS. 1A and 1B show an operating handle of a conventional delivery device 10 for manipulating a catheter assembly 20 in a patient. For some uses, such as installing an end of a pacemaker lead into cardiac tissue (or other cardiac catheter uses), it is necessary that a user have the ability to deflect or steer the distal tip of the catheter assembly 20 away from a longitudinal axis of the catheter assembly, and also to rotate the distal tip about a longitudinal axis of the catheter assembly. When using the conventional delivery device 10, a user may rotate the distal tip of the catheter assembly 20 about its longitudinal axis by rotating the user's hand and wrist to rotate the entire operating handle 30.

The hand and wrist rotation required to rotate the distal tip of the catheter assembly 20 about its longitudinal axis may result in shortcomings of the conventional delivery device 10 that can reduce the accuracy of or cause misuse of the device in a patient. As can be seen in FIG. 1B, rotating the user's hand and wrist may only permit a partial angular rotation A of the operating handle 30, since the wrist has a limited range of angular rotation. Also, a typical wrist rotation may result in the axis of rotation being misaligned with the longitudinal axis of the operating handle 30, so that the operating handle is translated and rotated during rotation of the wrist. If the operating handle 30 is translated during rotation, the distal tip of the catheter assembly 20 may also be translated within the patient, which may make it more difficult to accurately place the distal tip of the catheter assembly at a desired location within the patient, and which may result in unintended harmful contact between the distal tip of the catheter assembly and cardiac tissue.

Referring now to FIGS. 2A-2D to illustrate the structure and function of the present invention, an exemplary delivery device 100 for delivering into a patient an IMD lead 110 having a helical tip 112 has a catheter assembly 120 for delivering the IMD lead to and deploying the IMD lead at a target location. The helical tip 112 may be a helical, screw-in anchor that may be used to affix the IMD lead 110 to target tissue, such as the inside of the heart wall. In one example, the IMD lead 110 may be an Abbott Tendril MRI STS 2088 pacing lead. The delivery device 100 also includes an operating handle 130 for controlling deployment of the IMD lead 110 from the catheter assembly 120, for rotating the catheter assembly about a longitudinal axis of the catheter assembly (the first longitudinal axis L1), and for deflecting a distal end 121 of the catheter assembly away from the first longitudinal axis.

The catheter assembly 120 is configured to removably retain a distal portion of the IMD lead 110 at its distal end 121. The catheter assembly 120 includes an outer shaft 122 that is affixed at its proximal end to an insert 123 that is fixedly disposed inside the operating handle 130 by interference between features of the insert and the handle, such that the outer shaft is fixedly coupled to the operating handle. In particular, there may be interference between external features of the insert 123 and internal features of a nose 131 of the handle 130, which will be described below. The outer shaft 122 has a compartment therein configured to receive the distal portion of the IMD lead 110. The distal portion of the IMD lead 110 may be exposed by being advanced out of the outer shaft 122 and may be covered by being retracted into the outer shaft. The outer shaft 122 may be made of a flexible material such as nylon 11 or nylon 12, and it may have a round braid construction (i.e., round cross-section fibers braided together) or flat braid construction (i.e., rectangular cross-section fibers braided together), for example. A guide wire, a proximal end of the IMD lead 110, and/or mapping wires may extend through a lumen of the outer shaft 122 and into the operating handle 130.

Figure 2A:
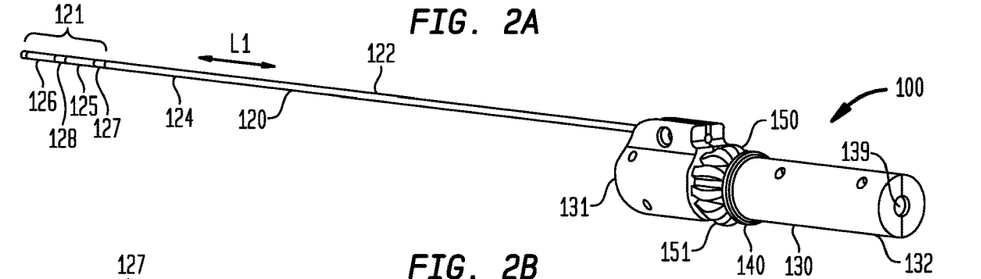
FIG. 2A is a perspective view of a delivery device for delivering an IMD lead into a patient, shown with the catheter assembly in a straight position.
Figure 2B:
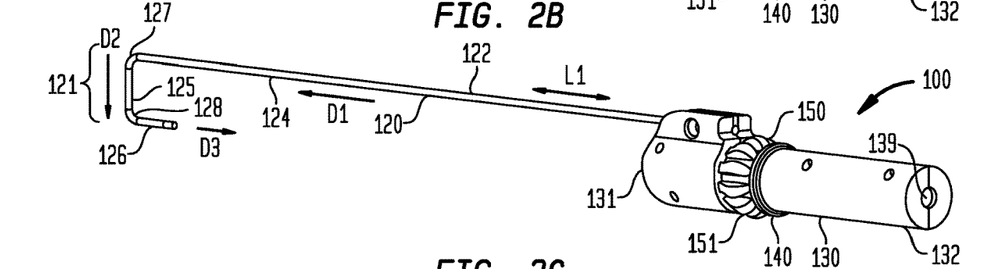
FIG. 2B is a perspective view of the delivery device of FIG. 2A, shown with the catheter assembly in a deflected position.
Figures 2C, 2D:
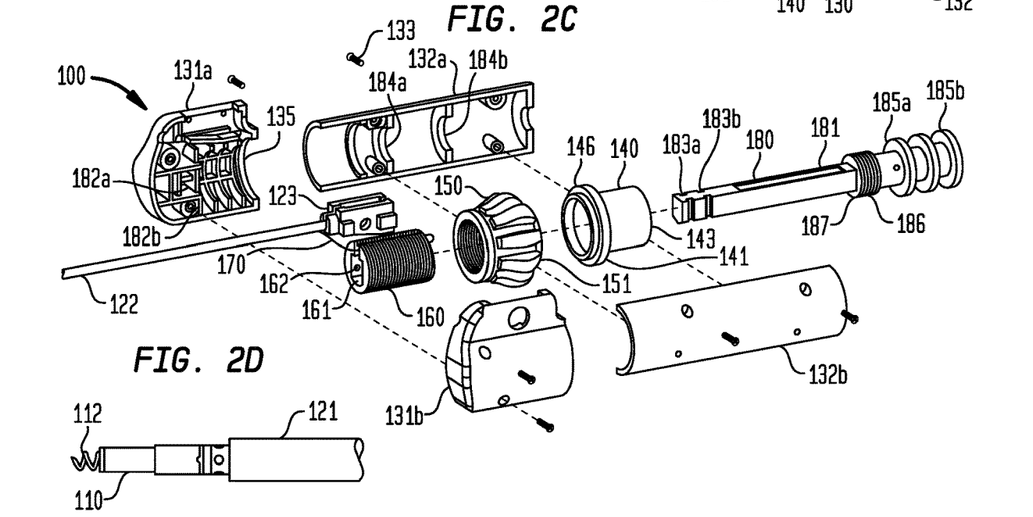
FIG. 2C is an exploded perspective view of the operating handle of the delivery device of FIG. 2A.
FIG. 2D is a side view of the distal end of the catheter assembly of the delivery device of FIG. 2A, shown with the distal portion of the IMD lead extending out of the catheter assembly.

The distal end 121 of the catheter assembly 120 is movable between a straight position shown in FIG. 2A, a deflected position shown in FIG. 2B, and any intermediate position between the straight position and the deflected position. In the straight position, the distal end 121 of the catheter assembly 120 is aligned with the longitudinal axis L1 of the catheter assembly. In the deflected position, the distal end 121 of the catheter assembly 120 can be deflected away from the longitudinal axis L1.

As shown in FIG. 2B, the distal end 121 of the catheter assembly 120 may have a "C" shape when disposed in the deflected position, in which a base segment 124 of the catheter assembly extends in a first direction D1 along the first longitudinal axis L1, a first segment 125 of the distal end 121 extends in a second direction D2 perpendicular to the first longitudinal axis, and a second segment 126 of the distal end extends in a third direction D3 perpendicular to the second direction and parallel to but opposite the first direction. The catheter assembly 120 may have a first weakened portion 127 disposed between the base segment 124 and the first segment 125 of the distal end 121, and a second weakened portion 128 disposed between the first segment and the second segment 126.

Although in the particular example shown in FIG. 2B, the second direction D2 is perpendicular to the first longitudinal axis L1, and the third direction D3 is opposite the first direction D1, that need not be the case. In other embodiments, the second and third directions D2 and D3 may have any angular orientation relative to one another and relative to the first direction DE In some examples, the number of segments comprising the distal end 121 of the catheter assembly 120 may be more or less than the two segments shown in FIGS. 2A and 2B, and the segments may have any length relative to one another. Although the distal end 121 of the catheter assembly 120 is shown as having a "C" shape in the deflected position, in other examples, the distal end may have any other deflected shape.

The first and second weakened portions 127, 128 may be less resistant to bending than the base segment 124, the first segment 125, and the second segment 126. The first and second weakened portions 127, 128 are configured to bend upon proximal retraction of a pull wire, which will be described below. The first and second weakened portions 127, 128 are biased towards the straight position shown in FIG. 2A, such that when tension on the pull wire is released, the first and second segments 125, 126 will return to the straight position i.e., in collinear alignment with the base segment 124. In one example, the first and second weakened portions 127, 128 may each include a memory metal therein that is biased to a straight position.

Figure 3A:
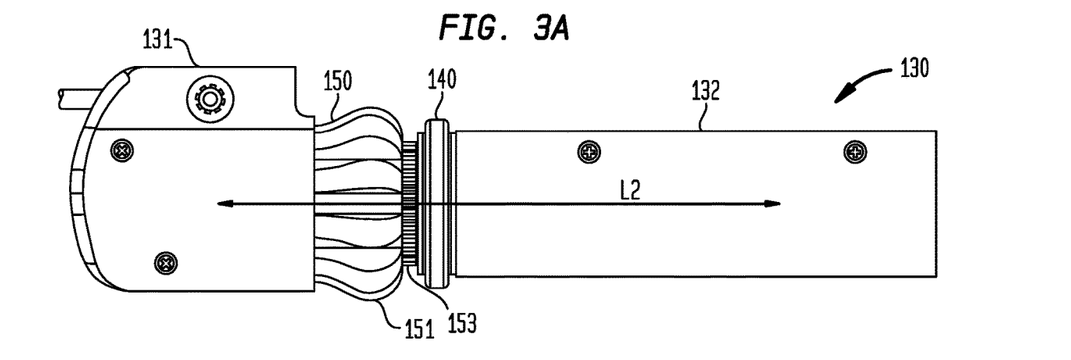
FIG. 3A is a side view of the operating handle of the delivery device of FIG. 2A, shown with the collar in a proximal position.
Figure 3B:
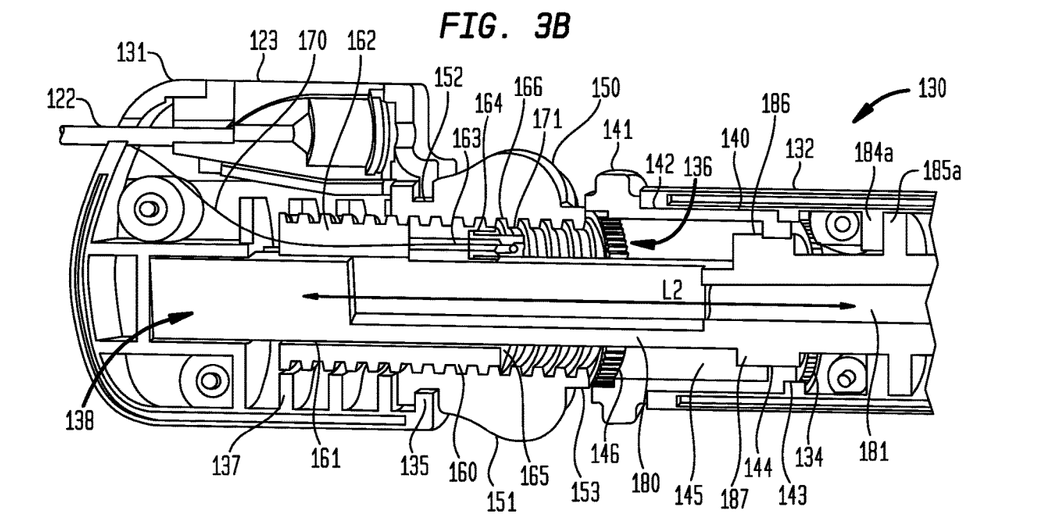
FIG. 3B is a longitudinal cross-section through a portion of the operating handle of FIG. 3A.
Figure 3C:
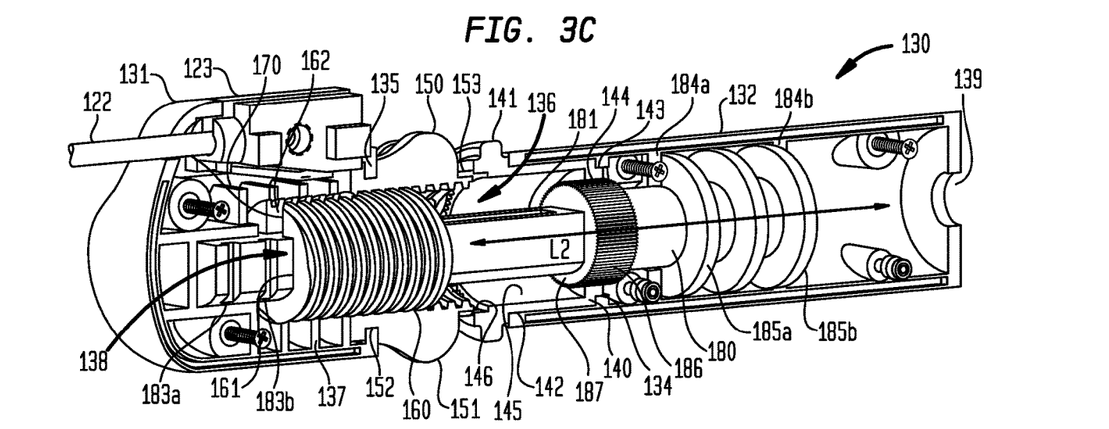
FIG. 3C is another longitudinal cross-section through the operating handle of FIG. 3A, shown in a perspective view.
Figure 4A:
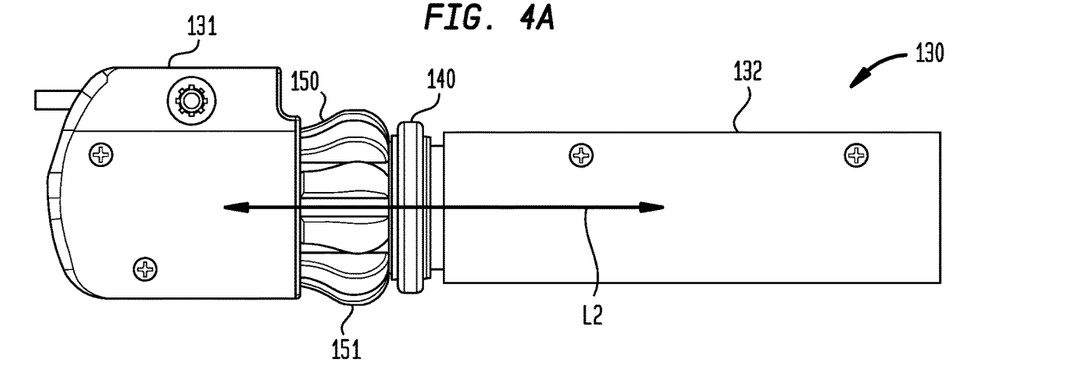
FIG. 4A is a side view of the operating handle of the delivery device of FIG. 2A, shown with the collar in a distal position.
Figure 4B:
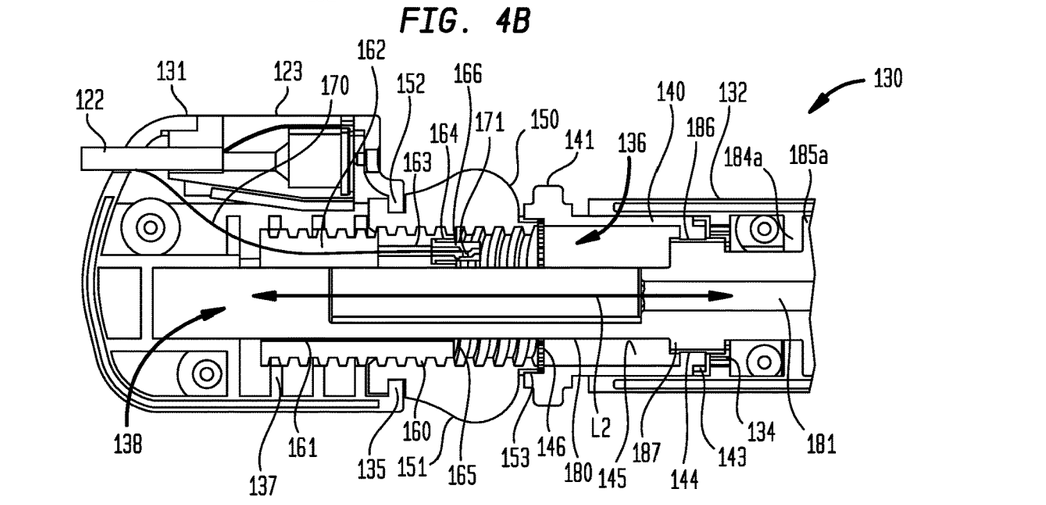
FIG. 4B is a longitudinal cross-section through a portion of the operating handle of FIG. 4A.
Figure 4C:
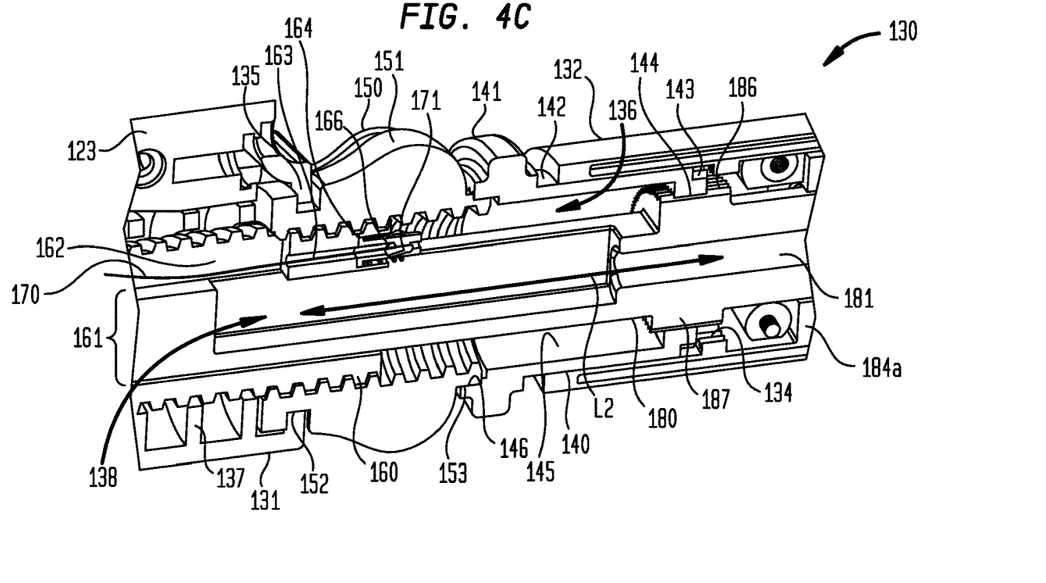
FIG. 4C is another longitudinal cross-section through a portion of the operating handle of FIG. 4A, shown in a perspective view.

The operating handle 130 is adapted to control the positioning of the distal end 121 of the catheter assembly 120, so that the distal end of an IMD lead 110 located in a compartment of the catheter assembly can be properly positioned for deployment into cardiac tissue, for example. The operating handle 130 may be toggled between a catheter deflection configuration, as shown in FIGS. 3A-3C, and a catheter rotation configuration, as shown in FIGS. 4A-4C. The operating handle 130 has a collar 140 that may be toggled proximally or distally to set the operating handle in the catheter deflection configuration or the catheter rotation configuration, respectively. A knob 150 of the operating handle 130 may be rotated about a longitudinal axis of the operating handle (the second longitudinal axis L2) to either deflect the distal end 121 of the catheter assembly 120 away from the first longitudinal axis L1 by retracting a screw 160 coupled to a pull wire 170, or to rotate the catheter assembly about the second longitudinal axis, depending on whether the collar 140 is in its proximal or distal position. The operating handle 130 may be configured to be operated by a single hand of a user. In such an embodiment, the collar 140 and the knob 150 may each be configured to be moved by only the thumb and index finger of a single hand of a user.

Returning to FIGS. 2A-2D, the operating handle 130 includes a nose 131 and a base 132. The nose 131 includes a left portion 131a and a right portion 131b. The left and right portions 131a and 131b may be individual pieces joined to one another as shown in FIG. 2A. The base 132 includes a left portion 132a and a right portion 132b. The left and right portions 132a and 132b may be individual pieces joined to one another as shown in FIG. 2A. Fasteners 133 may be used to join the left and right portions 131a, 131b to one another, and to join the left and right portions 132a, 132b to one another.

Referring to FIGS. 3A-3C, the collar 140 has a generally cylindrical shape and extends into a portion of an elongated space 136 within the base 132 of the operating handle 130. The collar 140 has an annular ring 141 defined on an outer surface 142 of the collar at the distal end of the collar. The ring 141 extends completely around the outer surface 142 of the collar 140 with its central axis coextensive with the second longitudinal axis L2. The ring 141 has an outer diameter that is greater than an inner diameter of the base 132, such that interference between the ring and a distal edge of the base prevents the ring from being completely inserted into the base.

The collar 140 has a first set of serrations 143 defined in the outer surface 142 at the proximal end of the collar, a second set of serrations 144 defined in an inner surface 145 of a reduced diameter portion at the proximal end of the collar, and a third set of serrations 146 defined in the inner surface of the collar at the distal end of the collar. The serrations 143 each extend adjacent to one another in a direction parallel to the second longitudinal axis L2 and completely around the outer surface 142. The serrations 144 each extend adjacent to one another in a direction parallel to the second longitudinal axis L2 and completely around the inner surface 145. The serrations 146 each extend adjacent to one another in a direction parallel to the second longitudinal axis L2 and completely around the inner surface 145.

The outer serrations 143 are configured to be selectively engageable in a mating configuration with corresponding serrations 134 defined in an inner surface of the handle base 132. The serrations 134 each extend adjacent to one another in a direction parallel to the second longitudinal axis L2 and completely around the inner surface of the base 132. When the collar 140 is in the proximal position shown in FIGS.

3A-3C, the outer serrations 143 are engaged with the inner serrations 134, such that the collar is rotationally locked relative to the base 132. When the collar 140 is moved to the proximal position, the range of motion of the collar along the second longitudinal axis is proximally limited by interference between the collar and the base 132. When the collar 140 is in the distal position shown in FIGS. 4A-4C, the outer serrations 143 are disengaged from the inner serrations 134, such that the collar may be rotated about the second longitudinal axis L2 relative to the base 132. When the collar 140 is moved to the distal position, the range of motion of the collar along the second longitudinal axis is distally limited by interference between the collar and the knob 150.

The knob 150 has a bulbous outer surface 151 that is configured to be easily grasped by the thumb and forefinger of a user and rotated in order to deflect the distal end 121 of the catheter assembly 120 in the catheter deflection configuration (FIGS. 3A-3C), or in order to rotate the catheter assembly and the handle nose 131 together in the catheter rotation configuration (FIGS. 4A-4C). The knob 150 is internally threaded for engagement with corresponding external threads of the screw 160, which will be described below. The knob 150 has a circumferential groove 152 defined in its outer surface 151 that is configured to engage a proximal flange 135 of the nose 131, so that the knob is constrained from translating relative to the nose along the second longitudinal axis L2, but is permitted to rotate about the second longitudinal axis relative to the nose unless the knob is rotationally locked relative to the nose by other components, as will be described below.

The knob 150 has serrations 153 defined in the outer surface 151 at the proximal end of the knob. The serrations 153 each extend adjacent to one another in a direction parallel to the second longitudinal axis L2 and completely around the outer surface 151. The outer serrations 153 are configured to be selectively engageable in a mating configuration with the inner serrations 146 at the distal end of the collar 140. When the collar 140 is in the proximal position shown in FIGS. 3A-3C, the outer serrations 153 are disengaged from the inner serrations 146, such that the knob 150 may be rotated about the second longitudinal axis L2 relative to the collar. When the collar 140 is in the distal position shown in FIGS. 4A-4C, the outer serrations 153 are engaged with the inner serrations 146, such that the knob 150 is rotationally locked relative to the collar.

The left and right portions 131a, 131b of the handle nose 131 and the left and right portions 132a, 132b of the handle base 132 collectively define the elongated space 136 in the operating handle 130 in which the screw 160 may travel. The elongated space 136 preferably permits the screw 160 to travel a distance that is at least as long as the anticipated length that the pull wire 170 affixed to the distal end 121 of the catheter assembly 120 needs to travel (e.g., about 12.7 mm or less), such that the distal end of the catheter assembly can be moved from the straight position to the fully deflected position. A series of ribs 137 in the left and right portions 131a, 131b of the nose 131 and the inner surface 145 of the collar 140 collectively define an enlarged bore 138 that is sized to freely and slidingly receive the screw 160. The enlarged bore 138 has an inner diameter slightly larger than the outer diameter of the screw 160.

The screw 160 extends along the second longitudinal axis L2 and is configured to remain threadedly engaged with the knob 150 throughout its range of travel. The screw 160 preferably is longer than the anticipated maximum travel distance of the screw within the elongated space 136 (e.g., at least about 25 mm), such that the screw does not fully disengage from the knob 150 during movement of the distal end 121 of the catheter assembly 120 between the straight position and the deflected position. The travel distance of the screw 160 within the elongated space 136 is limited in a distal direction by interference between the distal end of the screw 160 and a proximal-facing surface of a distalmost one of the ribs 137. The travel distance of the screw 160 is limited in a proximal direction by interference between the proximal end 165 of the screw 160 and a distal-facing surface of an axial shaft 180, which will be described below.

The screw 160 has a non-circular lumen 161 extending therethrough along the second longitudinal axis L2. The non-circular lumen 161 is configured to slidably receive the axial shaft 180 therethrough with minimal clearance. As shown in the figures, the non-circular lumen 161 has a generally square cross-section, but this need not always be the case. In other embodiments, the non-circular lumen 161 may have any cross-sectional shape that permits the axial shaft 180 to be rotationally locked relative to the screw 160, such as any regular or irregular polygon that is configured to slidably receive the axial shaft 180 therethrough with minimal clearance. As shown in the figures, the non-circular lumen 161 extends along the second longitudinal axis L2, but this need not always be the case. In other embodiments, the non-circular lumen 161 may have a central longitudinal axis that is offset from and parallel to the second longitudinal axis L2.

The screw 160 has a slot 162 extending radially inward from the threaded outer surface of the screw in a direction parallel to the second longitudinal axis L2. The slot is configured to provide a pathway for the pull wire 170 to extend into the screw 160, and a pathway for other wires from the catheter assembly 120 (e.g., mapping wires, not shown) to extend into a lumen 181 of the axial shaft 180 and out of the operating handle 130 through a proximal opening 139 in the handle base 132. The proximal end 171 of the pull wire 170 is affixed to the screw 160, so that the proximal end of the pull wire and the screw may translate proximally or distally together relative to the axial shaft 180.

The proximal end 171 of the pull wire 170 extends through a bore 163 that extends axially through the screw 160 between the slot 162 and a recess 164 extending into the proximal end 165 of the screw. The proximal end 171 of the pull wire 170 is affixed to an insert 166 that is removably engaged in the recess 164, so that the insert may be selectively affixed to the screw 160 for operative use, or removed from the screw so that the pull wire may be replaced. In the example shown in the figures, the proximal end 171 of the pull wire 170 is removably affixed to the screw 160 via engagement of the insert 166 in the recess 164, but that need not always be the case. In some embodiments, the proximal end of the pull wire may be directly affixed to the screw 160 without use of a removable insert.

The pull wire 170 is configured to deflect the distal end 121 of the catheter assembly 120 away from the first longitudinal axis L1 when the proximal end 171 of the pull wire is translated proximally. The pull wire 170 may be affixed to one side of a pull ring (not shown) that is disposed at the distal end 121 of the catheter assembly 120. The distal end 121 of the catheter assembly 120 may be biased towards the straight position shown in FIG. 2A, so when the proximal end 171 of the pull wire 170 is translated distally, thereby removing tension in the pull wire, the bias of the distal end of the catheter assembly may move the distal end to the straight position. Further details regarding how a pull wire may deflect a distal end of a catheter assembly may be found in U.S. Pat. No. 7,706,891, which is hereby incorporated by reference herein in its entirety.

The axial shaft 180 is configured to translationally fix the nose 131 and the base 132 of the handle 130 to one another while selectively permitting or preventing the nose from rotating relative to the base, depending on the position of the collar 140. The axial shaft 180 is translationally fixed to the nose 131 by the engagement of ribs 182a, 182b (FIG. 2C) formed in the left and right portions 131a, 131b of the nose with corresponding vertical slots 183a, 183b in side surfaces of the axial shaft. The axial shaft 180 is rotationally locked to the nose 131 by the engagement of the corresponding non-circular cross-sectional shapes of the distal end of the axial shaft and the ribs of the nose with minimal clearance therebetween.

The axial shaft 180 is translationally fixed to the base 132 by interference between distal and proximal ribs 184a, 184b (FIG. 2C) formed in the left and right portions 132a, 132b of the base and corresponding distal and proximal flanges 185a, 185b disposed at the proximal end of the axial shaft. The distance between the distal and proximal ribs 184a, 184b is slightly greater than the distance between the distal and proximal flanges 185a, 185b, such that interference between the distal rib and the distal flange prevents distal translation of the axial shaft 180 relative to the base 132, and interference between the proximal rib and the proximal flange prevents proximal translation of the axial shaft relative to the base.

An intermediate portion of the axial shaft 180 has an enlarged cylindrical disk 187 with serrations 186 formed around its outer surface. The serrations 186 each extend adjacent to one another in a direction parallel to the second longitudinal axis L2 and completely around the outer surface of the disk 187. The outer serrations 186 are configured to be permanently engaged in a mating configuration with the inner serrations 144 at the proximal end of the collar 140, regardless of the position of the collar. For example, when the collar 140 is in the proximal position of FIG. 3B, the inner serrations 144 at the proximal end of the collar are engaged with a proximal portion of the outer serrations 186, and when the collar is in the distal position of FIG. 4B, the inner serrations at the proximal end of the collar are engaged with a distal portion of the outer serrations of the disk 187.

As shown in the figures, the distal end of the axial shaft 180 has a generally square cross-section that corresponds to the shape of the lumen 161 extending through the screw 160. However, this need not always be the case. In other embodiments, the distal end of the axial shaft 180 may have any cross-sectional shape that permits the shaft to be rotationally locked relative to the screw 160, such as any regular or irregular polygon that is configured to be received within the non-circular lumen 161 with minimal clearance. As shown in the figures, the distal end of the axial shaft 180 extends along the second longitudinal axis L2, but this need not always be the case. In other embodiments, the distal end of the axial shaft 180 may have a central longitudinal axis that is offset from and parallel to the second longitudinal axis L2.

In operation, a user may selectively toggle the collar 140 between the proximal position of FIGS. 3A-3C, in which the knob 150 has freedom of rotation relative to all other components of the operating handle 130 while the screw 160 is at intermediate locations between the distal and proximal ends of its travel range, and the distal position of FIGS. 4A-4C, in which the knob is rotationally locked to all other components of the operating handle except for the base 132 of the handle. While the distal end 121 of the catheter assembly 120 is disposed in a patient, the user may freely toggle the collar 140 back and forth between the proximal and distal positions, depending on whether the user desires to deflect or straighten the distal end of the catheter assembly, or whether the user desires to rotate the catheter assembly about the second longitudinal axis L2 in order to change the direction of deflection of the distal end of the catheter assembly.

When the collar 140 is in the proximal position of FIGS. 3A-3C, the operating handle 130 is set in the catheter deflection configuration. Before insertion of the distal end 121 of the catheter assembly 120 into a patient, the catheter assembly will be in the straight position shown in FIG. 2A, and the screw 160 will be in its distalmost position. In this condition, the pull wire 170 will be in its distalmost position in which it does not exert any tension on the distal end 121 of the catheter assembly 120 to deflect same. If it is desired to deflect the distal end 121 of the catheter assembly 120 away from the first longitudinal axis L1, the user may grasp the knob 150 and rotate it clockwise from the perspective of the proximal end of the operating handle 130. In other embodiments, the thread orientation may be reversed so that the knob may be rotated counterclockwise to deflect the distal end 121 of the catheter assembly 120.

Due to the engagement of the threads of the knob 150 with the threads of the screw 160, the clockwise rotation of the knob will result in the screw being translated proximally along the axial shaft 180. Since the proximal end 171 of the pull wire 170 is affixed to the screw 160, proximal translation of the screw will proximally translate the pull wire, thereby beginning deflection of the distal end 121 of the catheter assembly 120.

While the knob 150 is rotating, the screw 160 will translate along the axial shaft 180 because the other components of the operating handle 130 are all rotationally locked to the axial shaft. In particular, the screw 160 is rotationally locked to the axial shaft 180 due to the engagement of the non-circular axial shaft into the non-circular lumen 161 of the screw, and the nose 131 is rotationally and translationally locked to the distal end of the axial shaft 180. The axial shaft 180 is translationally locked to the base 132 of the handle 130 due to the engagement of the flanges 185a, 185b of the axial shaft between the ribs 184a, 184b of the base. The axial shaft 180 is rotationally locked to the collar 140 due to the engagement of the outer serrations 186 of the disk 187 with the inner serrations 144 of the collar, and the collar is rotationally locked to the base 132 due to the engagement of the outer serrations 143 of the collar with the inner serrations 134 of the base.

The user may continue to rotate the knob 150 clockwise until the distal end 121 of the catheter assembly 120 is deflected to the desired position. To return the distal end 121 of the catheter assembly 120 to the straight position, the user may rotate the knob 150 counterclockwise, thereby advancing the screw 160 and the pull wire 170 distally along the axial shaft 180. As the pull wire 170 advances distally, it will tend to slacken, and the bias of the distal end 121 of the catheter assembly 120 will reduce the degree of deflection of the distal end to the degree permitted by the slackening of the pull wire. When the screw 160 is fully advanced to its distalmost position, the pull wire 170 will slacken sufficiently for the bias of the distal end 121 of the catheter assembly 120 to fully return the distal end of the catheter assembly to the straight position.

When the collar 140 is in the distal position of FIGS. 4A-4C, the operating handle 130 is set in the catheter rotation configuration. Before insertion of the distal end 121 of the catheter assembly 120 into a patient, the nose 131 of the operating handle 130 will be in an initial rotational orientation relative to the base 132, which may be the rotational orientation shown in FIG. 4A or any other rotational orientation.

If it is desired to rotate the catheter assembly 120 about the second longitudinal axis L2, the user may grasp the knob 150 and rotate it clockwise or counterclockwise, depending on which rotational orientation of the catheter assembly is desired. Due to the knob 150 being rotationally locked to all of the components except for the base 132, rotation of the knob will result in the catheter assembly 120, the nose 131, the screw 160, the axial shaft 180, and the collar 140 being rotated together about the second longitudinal axis L2 relative to the base. In particular, the knob 150 is rotationally locked to the collar 140 due to engagement between the outer serrations 153 of the knob and the inner serrations 146 of the collar. The collar 140 is rotationally locked to the axial shaft 180 due to the engagement of the inner serrations 144 of the collar with the outer serrations 186 of the disk 187. The axial shaft 180 is rotationally locked to the nose 131 and the screw 160 due to the non-circular axial shaft being received in a distal portion of the nose with minimal clearance, and being received through the non-circular lumen 161 of the screw with minimal clearance. The knob 150 is not rotationally locked to the base 132 since the outer serrations 143 of the collar 140 are not engaged with the inner serrations 134 of the base.

Although the longitudinal axis L1 of the catheter assembly 120 is laterally offset from the second longitudinal axis L2, the small amount of the offset relative to the length of the catheter assembly will likely result in only a small amount of longitudinal translation of the catheter assembly as it is rotated about the second longitudinal axis, compared to the larger longitudinal translation that may result when rotating the catheter assembly 20 of FIG. 1A. Once the user is satisfied with the rotational orientation of the catheter assembly 120, the user may slide the collar 140 to the proximal position of FIGS. 3A-3C, thereby rotationally decoupling the knob 150 from the nose 131, which may prevent the user from unintentionally changing the rotational orientation of the nose relative to the base 132.

Compared to the conventional delivery device 10, the delivery device 100 may permit a user to execute fine rotation of the catheter assembly 120 about the second longitudinal axis L2 while more easily maintaining hand position on the operating handle 130, thereby minimizing longitudinal translation of the catheter assembly during such fine rotation. In contrast, a user may not be able to use his or her wrist to rotate the conventional delivery device 10 a full 360 degrees without changing how he or she is gripping the operating handle 30. Therefore, if a user of the conventional delivery device 10 needs to change hand grip while rotating the operating handle 30, this may result in significant unintended longitudinal translation of the catheter assembly 20 that may be greater than the minimal longitudinal translation of the catheter assembly 120 during rotation of the nose 131 of the operating handle 130.

Although the embodiments herein have been described as being configured to deliver a distal end of an IMD lead 110, such as a pacing lead, any of the operating handles and methods described herein may be incorporated into any other type of medical device where fine control of deflection and rotation of the distal end of a catheter is desired. For example, the devices described herein can be modified to deliver any prosthetic device into a patient in a compartment that is covered by a distal sheath similar to those described herein. In some embodiments, the implantable medical device may be a leadless device entirely contained within the distal end 121 of the catheter assembly 120 before deployment into a patient. In other examples, the devices described herein can be configured to deliver an expandable heart valve such as a prosthetic aortic valve or a prosthetic mitral valve to a target location in a patient. Such a prosthetic heart valve may be radially compressed and contained within the distal end 121 of the catheter assembly 120, and the prosthetic heart valve may be deflected and rotated for placement at a desired location, such as a native aortic or mitral valve annulus.

In particular embodiments, the operating handles described herein can be configured to manipulate other types of catheters, so that deflection and rotation of the distal end of the catheter may be finely controlled. In one example, the operating handles described herein may be configured to manipulate the distal end of an ablation catheter, so that energy may be delivered to anatomical structures (e.g., tissue to be ablated) at desired locations within a patent. In another example, the operating handles described herein may be configured to manipulate the distal end of a mapping catheter, so that desired locations within anatomical structures (e.g., arteries, veins, organs, etc.) within a patent may be imaged.

Although the serrations 134, 143, 144, 146, 153, and 186 are described herein as each extending adjacent to one another in a direction parallel to the second longitudinal axis L2 and completely around the second longitudinal axis, that need not always be the case. Any or all of the pairs of serrations 134/143, 146/153, and 144/186 may have any complimentary shape with one another, so long as they permit the two engaged components to translate relative to one another while being rotationally locked relative to one another when engaged. For example, any of the pairs of serrated components may each contain only a few complimentary teeth spaced apart about the second longitudinal axis L2, or any of the pairs of serrated components may have their serrations replaced with one or more pins configured to engage with one or more complimentary recesses having any spacing about the second longitudinal axis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

In summary, the disclosure herein describes multiple embodiments of a delivery device for an implantable medical device. The delivery device may include a catheter assembly having a proximal end, a distal end, and a compartment at the distal end for retaining the implantable medical device. The catheter assembly may extend along a first longitudinal axis. The catheter assembly may have a pull wire extending therethrough. A distal end of the pull wire may be affixed to the distal end of the catheter assembly. The delivery device may include an operating handle extending along a second longitudinal axis.

The operating handle may include a nose affixed to a proximal end of the catheter assembly, an axial shaft having a distal end affixed to the nose and a proximal end, a base translationally fixed to the proximal end of the axial shaft, a screw having external threads and a non-circular lumen, a knob having internal threads engaged with the external threads of the screw, the knob being translationally fixed to the nose, and a collar extending at least partially around the axial shaft in a circumferential direction. The axial shaft may extend along the second longitudinal axis. The axial shaft may extend through the non-circular lumen so that the screw is translatable along the axial shaft and nonrotatable relative to the axial shaft. A proximal end of the pull wire may be affixed to the screw.

The collar may be rotationally fixed to the nose, the axial shaft, and the screw. The collar may be translatable between a proximal position and a distal position. With the collar in the proximal position, the knob may be rotatable relative to the collar and the collar may be nonrotatable relative to the base, so that rotation of the knob about the second longitudinal axis results in deflection of the distal end of the catheter assembly away from the first longitudinal axis. With the collar in the distal position, the base may be rotatable relative to the collar and the collar may be nonrotatable relative to the knob, so that rotation of the knob about the second longitudinal axis results in rotation of the catheter assembly about the second longitudinal axis; and/or the second longitudinal axis may be laterally offset from the first longitudinal axis in a direction transverse to the first longitudinal axis; and/or the collar and the knob each may have complementary serrations therein, and when the collar is in the distal position, the serrations of the collar may be engaged with the serrations of the knob; and/or the collar and the base each may have complementary serrations therein, and when the collar is in the proximal position, the serrations of the collar may be engaged with the serrations of the base; and/or the collar and the axial shaft each may have complementary serrations therein, and the serrations of the collar may be permanently engaged with the serrations of the axial shaft; and/or the range of motion of the collar along the second longitudinal axis may be distally limited by interference between the collar and the knob, and may be proximally limited by interference between the collar and the base; and/or the nose, the screw, the knob, the collar, and the base each may extend completely circumferentially around a respective longitudinal portion of the axial shaft; and/or a lumen may extend at least partially through the axial shaft along the second longitudinal axis, the catheter assembly and the lumen of the axial shaft together being configured to receive a mapping wire therethrough.

Also described herein are multiple embodiments of an operating handle configured to be coupled to a catheter assembly. The operating handle may include a nose configured to be affixed to a proximal end of the catheter assembly, an axial shaft having a distal end affixed to the nose, a proximal end, and a longitudinal axis, a base translationally fixed to the proximal end of the axial shaft, a screw having external threads and a non-circular lumen, a knob having internal threads engaged with the external threads of the screw, and a collar extending at least partially around the axial shaft in a circumferential direction. The axial shaft may extend through the non-circular lumen so that the screw is translatable along the axial shaft and nonrotatable relative to the axial shaft. The knob may be translationally fixed to the nose.

The collar may be rotationally fixed to the nose, the axial shaft, and the screw. The collar may be translatable between a proximal position and a distal position. With the collar in the proximal position, the knob may be rotatable relative to the collar and the collar may be nonrotatable relative to the base, so that rotation of the knob about the longitudinal axis results in translation of the screw along the axial shaft. With the collar in the distal position, the base may be rotatable relative to the collar and the collar may be nonrotatable relative to the knob, so that rotation of the knob about the longitudinal axis results in rotation of the nose, the axial shaft, the screw, and the collar relative to the base; and/or the collar and the knob each may have complementary serrations therein, and when the collar is in the distal position, the serrations of the collar may be engaged with the serrations of the knob; and/or the collar and the base each may have complementary serrations therein, and when the collar is in the proximal position, the serrations of the collar may be engaged with the serrations of the base; and/or the collar and the axial shaft each may have complementary serrations therein, and the serrations of the collar may be permanently engaged with the serrations of the axial shaft; and/or the range of motion of the collar along the longitudinal axis may be distally limited by interference between the collar and the knob, and may be proximally limited by interference between the collar and the base; and/or the nose, the screw, the knob, the collar, and the base each may extend completely circumferentially around a respective longitudinal portion of the axial shaft.

Further described herein are multiple embodiments of a method of moving a catheter assembly with an operating handle. The method may include providing the catheter assembly and the operating handle. The operating handle may have a nose affixed to a proximal end of the catheter assembly, an axial shaft having a distal end affixed to the nose, a base translationally fixed to a proximal end of the axial shaft, a screw having external threads and a non-circular lumen, the axial shaft extending through the non-circular lumen, a pull wire extending from the screw to a distal end of the catheter assembly, a knob having internal threads engaged with the external threads of the screw, and a collar extending at least partially around the axial shaft in a circumferential direction.

The method may include moving the collar to a distal position relative to the base. The method may include, while the collar is in the distal position, rotating the knob in a first direction to rotate the catheter assembly, the nose, the axial shaft, the screw, and the collar relative to the base. The method may include moving the collar to a proximal position. The method may include, while the collar is in the proximal position, rotating the knob in the first direction to pull the pull wire in a proximal direction, thereby deflecting the distal end of the catheter assembly away from a longitudinal axis of the catheter assembly; and/or the collar and the knob each may have complementary serrations therein, and moving the collar to the distal position may engage the serrations of the collar with the serrations of the knob to rotationally lock the collar to the knob; and/or the collar and the base each may have complementary serrations therein, and moving the collar to the proximal position may engage the serrations of the collar with the serrations of the base to rotationally lock the collar to the base; and/or the collar and the axial shaft each may have complementary serrations therein, the serrations of the collar being permanently engaged with the serrations of the axial shaft so that the collar is rotationally locked to the axial shaft; and/or when the collar is moved to the distal position, the collar may be distally limited by interference between the collar and the knob, and when the collar is moved to the proximal position, the collar may be proximally limited by interference between the collar and the base; and/or the nose, the screw, the knob, the collar, and the base each may extend completely circumferentially around a respective longitudinal portion of the axial shaft.

The invention claimed is:

1. An operating handle configured to be coupled to a catheter assembly, the operating handle comprising:
   a nose configured to be affixed to a proximal end of the catheter assembly;
   an axial shaft having a distal end affixed to the nose, a proximal end, and a longitudinal axis;
   a base translationally fixed to the proximal end of the axial shaft;
   a screw having external threads and a non-circular lumen, the axial shaft extending through the non-circular lumen so that the screw is translatable along the axial shaft and nonrotatable relative to the axial shaft;
   a knob having internal threads engaged with the external threads of the screw, the knob being translationally fixed to the nose; and
   a collar extending at least partially around the axial shaft in a circumferential direction, the collar being rotationally fixed to the nose, the axial shaft, and the screw, the collar being translatable between a proximal position and a distal position;
   with the collar in the proximal position, the knob being rotatable relative to the collar and the collar being nonrotatable relative to the base, so that rotation of the knob about the longitudinal axis results in translation of the screw along the axial shaft, and
   with the collar in the distal position, the base being rotatable relative to the collar and the collar being nonrotatable relative to the knob, so that rotation of the knob about the longitudinal axis results in rotation of the nose, the axial shaft, the screw, and the collar relative to the base.

2. The operating handle of claim 1, wherein the collar and the knob each have complementary serrations therein, and when the collar is in the distal position, the serrations of the collar are engaged with the serrations of the knob.

3. The operating handle of claim 1, wherein the collar and the base each have complementary serrations therein, and when the collar is in the proximal position, the serrations of the collar are engaged with the serrations of the base.

4. The operating handle of claim 1, wherein the collar and the axial shaft each have complementary serrations therein, and the serrations of the collar are permanently engaged with the serrations of the axial shaft.

5. The operating handle of claim 1, wherein the range of motion of the collar along the longitudinal axis is distally limited by interference between the collar and the knob, and is proximally limited by interference between the collar and the base.

6. The operating handle of claim 1, wherein the nose, the screw, the knob, the collar, and the base each extend completely circumferentially around a respective longitudinal portion of the axial shaft.

* * * * *